United States Patent
Skalsky et al.

(10) Patent No.: US 9,107,451 B2
(45) Date of Patent: Aug. 18, 2015

(54) COATING COMPOSITION FOR THE DIP COATING OF CAPSULE HALVES

(75) Inventors: Brigitte Skalsky, Groβ-Gerau (DE);
Manfred Aβmus, Bickenbach (DE);
Odette Hensel, Weiterstadt (DE);
Hans-Ulrich Petereit, Darmstadt (DE)

(73) Assignee: Evonik Röhm GmbH, Darmstadt (DE)

( * ) Notice: Subject to any disclaimer, the term of this patent is extended or adjusted under 35 U.S.C. 154(b) by 834 days.

(21) Appl. No.: 12/845,994

(22) Filed: Jul. 29, 2010

(65) Prior Publication Data
US 2011/0033530 A1    Feb. 10, 2011

Related U.S. Application Data

(60) Provisional application No. 61/229,537, filed on Jul. 29, 2009.

(51) Int. Cl.
| | | |
|---|---|---|
| *A61K 9/64* | (2006.01) | |
| *A23P 1/04* | (2006.01) | |
| *A23L 1/00* | (2006.01) | |
| *A61K 9/48* | (2006.01) | |
| *A61K 47/32* | (2006.01) | |

(52) U.S. Cl.
CPC .............. *A23P 1/04* (2013.01); *A23L 1/0029* (2013.01); *A61K 9/4891* (2013.01); *A61K 47/32* (2013.01)

(58) Field of Classification Search
USPC ........................................................ 424/456
See application file for complete search history.

(56) References Cited

U.S. PATENT DOCUMENTS

| | | | | |
|---|---|---|---|---|
| 4,040,536 | A * | 8/1977 | Schwarz ........................... | 220/8 |
| 4,138,013 | A * | 2/1979 | Okajima ......................... | 206/528 |
| 5,326,586 | A * | 7/1994 | Grabowski et al. ........... | 427/487 |
| 6,287,594 | B1 | 9/2001 | Wilson et al. | |
| 7,429,619 | B2 * | 9/2008 | Kamath ...................... | 514/772.1 |
| 7,498,044 | B2 | 3/2009 | Petereit et al. | |
| 2004/0142035 | A1 | 7/2004 | Chang et al. | |
| 2005/0079210 | A1 | 4/2005 | Gupta | |
| 2010/0226978 | A1 | 9/2010 | Petereit et al. | |
| 2011/0020441 | A1 | 1/2011 | Klaveness et al. | |

FOREIGN PATENT DOCUMENTS

| | | |
|---|---|---|
| CN | 1046459 A | 10/1990 |
| EP | 0 393 747 A2 | 10/1990 |
| EP | 0 393 747 A3 | 10/1990 |
| JP | 59-155325 A | 9/1984 |
| JP | 3-2119 A | 1/1991 |
| JP | 10-203964 A | 8/1998 |
| JP | 2002-509103 A | 3/2002 |
| JP | 2006-524643 A | 11/2006 |
| WO | 03/072087 | 9/2003 |
| WO | 2004/096185 | 11/2004 |
| WO | WO 2009/036812 A1 | 3/2009 |
| WO | WO 2009/074811 A2 | 6/2009 |
| WO | WO 2009/074811 A3 | 6/2009 |

OTHER PUBLICATIONS

Hogan (Film-coating materials and their properties; Pharmaceutical Coating Technology, 1995, Informa Healthcare).*
Chen (J Pharm Innov (2008) 3:3-14; published online Mar. 7, 2008).*
Interview agenda for Sep. 5, 2013 interview (Sep. 3, 2013).*
International Search Report issued Jun. 30, 2011, in PCT/EP2010/058370.
Nathalie Huyghebaert, et al., "In vitro evaluation of coating polymers for enteric coating and human ileal targerting", International Journal of Pharmaceutics, vol. 298, XP 4943736, Jul. 14, 2005, pp. 26-37.
"Guidelines for Formulation Development and Process Technology for Enteric Coatings", Pharma Polymers, http://www.pharma-polymers.com/NR/rdonlyres/1EA56E7C-0D38-4084-8DF9-53F9B484FD5D/0/31eGuidelinesforFormulationDevelopmentandProcessTechnology forEntericCoatings.pdf, XP 2560458, Mar. 2009, pp. 1-3.
Manfred Assmus, et al., "Accurate GI Targeting with EUDRAGIT FS 30 D/L 30 D-55 Mixtures", http://www.pharma-polymers.com/pharmapolymers/MCMSbase/Pages/ProvideResource.aspx?respath=/NR/rdonlyres/32DDD09C-18F5-47A0-AFFA-0020E84F9C57/0/CRS2008_AccurateGITargetingwithEUDRAGITS30DandL30D55mixtures.pdf, XP 2560459, 2008, 2 pages.
Nathalie Huyghebaert, et al.; Alternative Method for Enteric Coating of HPMC Capsules Resulting in Ready-to-use enteric-coated Capsules; received in revised form Nov. 28, 2003; accepted Jan. 7, 2004; pp. 617-623.

(Continued)

*Primary Examiner* — Peter J Reddig
*Assistant Examiner* — Devang Thakor
(74) *Attorney, Agent, or Firm* — Oblon, McClelland, Maier & Neustadt, L.L.P.

(57) ABSTRACT

A coating composition for the enteric coating of capsule halves made of water-soluble or water-swellable polymer material in a dipping process is provided. The composition is an aqueous dispersion or solution, containing a polymer mixture of at least one first (meth)acrylate copolymer, which is enteric, and at least one further (meth)acrylate copolymer, which is enteric or water-insoluble, and also auxiliaries which influence the viscosity of the dispersion and the elasticity of the dried polymer film. The solids content of the dispersion or solution is more than 25% by weight and the viscosity is 150 to 1500 mPa·s and a dried film produced from the dispersion or solution has an elongation at break of at least 200%. Also provided is a capsule composed of two capsule halves coated with the dispersion or solution in a dipping process does. The enteric capsule does not dissolve in 0.1 N HCl at pH 1.2 after two hours, but completely dissolves in buffer at pH 6.8 in less than 30 minutes. A method to prepare enteric coated capsule halves is also provided.

27 Claims, No Drawings

(56) References Cited

OTHER PUBLICATIONS

Office Action issued Nov. 9, 2012 in European Patent Application No. 10 724 857.7.

Japanese Office Action issued Feb. 24, 2014 in Patent Application No. 2012-522057 (English Translation only).

Combined Office Action and Search Report issued Dec. 19, 2012 in Chinese Patent Application No. 201080022662.9.

Zhang, Xiangrong, et al., Water Vapor Permeability of Free Film of Eudragit® NE 30 D Blended with Eudragit® L 30D-55, China Pharmaceuticals, vol. 15, No. 15, 6 pages submitting English translation only, Dec. 31, 2006.

* cited by examiner

COATING COMPOSITION FOR THE DIP COATING OF CAPSULE HALVES

BACKGROUND OF THE INVENTION

1. Field of the Invention

The invention relates to a coating composition for the enteric coating of capsule halves made of water-soluble or water-swellable polymer material in the dipping process.

2. Description of the Related Art

Huyghebaert et al., *European Journal of Pharmaceutical Sciences* 21 (2004) 617-623, describe an alternative method for the enteric coating of capsules made of hydroxypropylmethylcellulose (HPMC) in which ready-to-use enteric capsule parts are obtained.

In the introductory section, it is reported that enteric coated HPMC capsules have for a long time been used in the dietetic food supplement industry as vegetarian alternatives to gelatine. It is also mentioned that although the enteric coating of hard gelatine capsules made of organic solutions is possible, it is difficult to execute and may lead to embrittlement of the capsules, which can result in poor adhesion of the coating. This can be overcome by applying an intermediate layer, although this is lengthy and complicated. Moreover, coating processes from aqueous preparations have the advantage over conventional coating processes in that gelatine capsules from organic solutions may be of concern on account of the toxicological and safety aspects. The coating of gelatine capsules from aqueous preparations, however, is very demanding and requires long processing times because of the solubility of the gelatine in water, which overall leads to high costs.

It is furthermore reported that, in contrast to gelatine capsules, HPMC capsules can be enteric coated relatively easily from aqueous preparations. However, it is necessary to additionally apply a sealing between the capsule halves, e.g. through a gelatine solution to be applied manually, in order to avoid an untightness of the capsule and an uncontrolled escape of the contents in the stomach. Another technique is to apply water/ethanol mixtures between the capsule halves and to weld the parts together at 40-60° C.

Using aqueous preparations (EUDRAGIT® FS 30 D, EUDRAGIT® L 30 D-55, Aquoat® AS-HF or Sureteric®) based on (meth)acrylate copolymers or polyvinyl acetate phthalate, plasticizers such as triethyl citrate and further auxiliaries, such as, for example, talc, it is possible to provide HPMC capsules with an enteric film. A separate sealing step can be dispensed with in the case of this coating technology. In particular, HPMC capsules which have been coated with (meth)acrylate copolymers are depicted as particularly advantageous am the sum of their properties.

It is furthermore mentioned that the dipping process for the enteric coating of capsules is very time-consuming and can bring with it a multitude of practical problems. In particular, the problems consist in an uneven coating and unsatisfactory enteric properties.

Problem and Solution

Capsules filled with active ingredients or food constituents, in particular made of gelatine or hydroxypropylmethylcellulose, have been used for a long time in the fields of pharmacy, food supplements and cosmetics. Active ingredients are to be understood as meaning in particular pharmaceutical active ingredients, food supplements or active ingredients with an assumed cosmetic effect, so-called cosmeculticals. Enteric coatings which are intended to prevent the capsule contents from being released in the stomach have likewise been known for a long time. Whereas capsule halves e.g. made of gelatine are produced with high precision in the dipping process, the enteric coatings for such capsules are produced almost exclusively in the spraying process. Attempts to apply enteric coatings in the dipping process have hitherto proven unsatisfactory.

DETAILED DESCRIPTION OF THE INVENTION

Therefore, an object of the invention is to provide a coating composition for the enteric coatings of capsule halves which can be applied in the dipping process. Furthermore, the coating composition should comprise no organic solvents. The coating composition should ensure the tightness of the closed capsules in the gastric juice without the capsules requiring an additional sealing. The coating composition should have adequate flowability in order to be able to be applied in the dipping process, but at the same time permit short drying times. The dried coating should be sufficiently elastic and have a uniform coating thickness. In the milieu of the intestine, rapid dissolution of the capsules should take place.

This and other objects have been achieved by the present invention, the first embodiment of which provides an enteric coating composition, comprising:

a polymer mixture of at least one first enteric (meth)acrylate copolymer and at least one further enteric or water soluble (meth)acrylate copolymer; and at least one auxiliary;

wherein the composition is a solution or dispersion of the polymer mixture having a solids content more than 25% by weight, a viscosity of the composition is from 150 to 1500 mPa·s, and an elasticity of a film produced from the enteric coating composition has an elongation at break of at least 200%.

In a second embodiment, the invention provides an enteric capsule, comprising:

two joined capsule halves and a coating on each capsule half;

wherein the coating comprises a polymer mixture of at least one first enteric (meth)acrylate copolymer and at least one further enteric or water soluble (meth)acrylate copolymer; and at least one auxiliary;

the coating has an elasticity measured by elongation at break of at least 200%, and the capsule does not dissolve in 0.1 N HCl at pH 1.2 after two hours, but does dissolve completely in a buffer solution at pH 6.8 in less than 30 minutes.

In a third embodiment the invention provides a method for preparing an enteric coated capsule half, comprising:

dipping an uncoated capsule half on a dipstick into an enteric coating composition to obtain an enteric coated capsule half;

removing the stick with the enteric coated capsule halve from the enteric coating composition, drying the enteric coating composition;

cutting off the enteric coated capsule half; and removing the enteric coated capsule half from the stick;

wherein the enteric coating composition comprises a polymer mixture of at least one first enteric (meth)acrylate copolymer and at least one further enteric or water soluble (meth)acrylate copolymer; and at least one auxiliary;

the enteric coating composition is a solution or dispersion of the polymer mixture having a solids content more than 25% by weight, a viscosity of the composition is from 150 to 1500 mPa·s, and an elasticity of a film produced from the enteric coating composition has an elongation at break of at least 200%.

Capsule Halves and Capsules

Capsule halves may be the upper or lower parts of a capsule. The upper and lower parts fit together such that they may be engaged in one another in a locking manner and form a closed capsule. A capsule thus consists of an upper and a lower half which can be filled as required as a container with an active ingredient and then may be firmly closed by engaging with the upper part. Filled capsules are provided in particular for oral application. Capsules e.g. made of gelatine without an enteric coating dissolve in the stomach.

Capsule halves, upper or lower parts, consist in particular of a water-soluble or water-swellable polymer material. Both capsule halves preferably consist of gelatine or of hydroxypropylmethylcellulose. Preference is given to gelatine. Less customary, but also possible material for capsule halves are polymers such as, for example, starch, pectin or agar.

As a rule, a capsule consists of a uniform material, in particular of the same or identical material. Consequently, preferably both capsule halves, upper and lower halves, consist e.g. uniformly of gelatine, in particular of the same or identical gelatine.

Capsules and capsule halves made of water-soluble or water-swellable polymer material are used widely for administering pharmaceutical active ingredients or food supplements. In particular, mention may be made of the fields of pharmacy and food supplements (nutraceuticals), where the field of cosmetics, as far as food supplements or potential active ingredients (cosmeceuticals) are concerned, may be included.

The capsule halves are enteric coated. "Enteric coated" means that the capsule halves have been enteric coated on their exterior. A closed capsule may therefore be protected externally from dissolution in gastric juice, pH 1 to about 5. The enteric coating rapidly dissolves in the area of the intestinal fluid, above pH 5, meaning that the underlying capsule material likewise dissolves and releases the contents of the capsule.

A capsule composed of two capsule halves enteric coated with the dispersion or solution in the dipping process does not dissolve in 0.1 N HCl (artificial gastric fluid according to USP without the addition of enzyme) at pH 1.2 after 2 hours, then dissolve completely in buffer at pH 6.8 according to USP, either after rebuffering the pH 1.2 medium to pH 6.8 or by transferring the capsule to the pH 6.8 buffer. Suitable testing methods are known to the person skilled in the art and can be found, for example, in USP 32. The capsules are held under the surface of the liquid using sinkers.

Dimension of Capsules

Within the context of the invention, a closed capsule may have a total length in the range from about 5 to 50 mm including all lengths and sub-lengths therebetween. The diameter of the upper part can be in the range from about 4 to 12 mm including all lengths and sub-lengths therebetween. The diameter of the lower part can be in the range from about 2 to 10 mm including all lengths and sub-lengths therebetween. The length of the upper part may be in the range from about 4 to 20 mm and that of the lower part in the range from 8 to 30 mm. The fill volume can be between about 0.1 and 2 ml including all volumes therebetween.

Capsules may be divided, for example, into standardized sizes from 000 to 5 (see in this context e.g.: Fahrig W. and Hofer U. (1983): *Die Kapsel, Grundlagen, Technologie and Biopharmazie einer modernen Arzneiform* [Capsules, Principles, Technology and Biopharmacy of a Modern Drug Form], Wissenschaftliche Verlagsgesellschaft mbH Stuttgart).

A closed capsule of size 000 has, for example, a total length of about 28 mm for a diameter of the upper part of about 9.9 mm and a diameter of the lower part of about 9.5 mm. The length of the upper part is about 14 mm, that of the lower part 22 mm. The fill volume is about 1.4 ml.

A closed capsule of size 5 has, for example, a total length of about 10 mm for a diameter of the upper part of about 4.8 mm and a diameter of the lower part of about 4.6 mm. The length of the upper part is about 5.6 mm, that of the lower part 9.4 mm. The fill volume is about 0.13 ml.

Layer Thicknesses

The coating composition according to the invention is preferably adjusted so that, in the dried state, coating films with layer thicknesses in the range from 20 to 100 including all thicknesses therebetween, in particular 40 to 80 µm, are produced. In this connection, the capsule halves can already be produced such that the wall thicknesses on the outside are in each case reduced by the layer thickness of the enteric coating to be expected, such that standard wall thicknesses arise again following the dip coating. If, for example, a customary standard capsule upper part and lower part made of gelatine has a wall thickness of 100 µm, then the wall thicknesses for enteric coated capsules are reduced in the preparation to e.g. ca. 60 µm. Then, in the dipping process, an enteric coating with a layer thickness in the dried state of ca. 40 µm is applied. The resulting upper and lower parts then again have wall thicknesses of 100 µm and can be further processed in the same way as standard capsules without altering the machine settings.

Sealing Function of the Enteric Coating

As a result of the preparation in dipping processes, the lower capsule half, the lower part, receives a continuous enteric coating which, in the closed state, is partly overlapped by the upper part. Favoured by the elasticity of the film and its uniformity, the overlapped part of the enteric coating assumes here a sealing function which effectively prevents the penetration of gastric fluid through a possible gap between the lower part and the upper part. The dipping process may thus offer an advantage over the coating of closed capsules in a spraying process in which no overlapping occurs, as a result of which the abutment point on the edge of the upper part always brings with it the potential risk of untightness. In many cases, therefore, prior to the enteric coating of closed capsules in a spraying process, a sealing band is applied or another measure is undertaken for sealing the abutment point. Measures of this kind can be dispensed with when applying the coating composition according to the invention in the dipping process, which represents a further advantage.

The tightness of the capsule material may be demonstrated, for example, by pouring a marker, e.g. a lye or an active ingredient that is easy to detect and readily soluble in water, into the coated capsule halves or into the capsule and observing its escape into the medium or its retention in the capsule during the incubation for 2 hours in 0.1 N HCl or in artificial gastric fluid pH 1.2 in accordance with USP. Here, no or only a very small part of the marker should be detectable in the medium, less than 10%.

Aqueous Dispersion or Solution

The coating composition according to the invention may be in the form of an aqueous dispersion or solution. The term "aqueous dispersion or solution" is understood in the broad sense and is intended to include all transition states, in particular also so-called polymer/colloidal solutions. The aqueous dispersion consists of a solid phase and a liquid phase. The solids phase and the liquid phase total 100% by weight.

The liquid phase of the aqueous dispersion or solution may be based essentially or completely on the dispersant or solvent water. The liquid phase thus consists of at least 95% by weight, preferably at least 98% by weight, in particular 100% by weight, of water. Organic solvents, such as, for example, ethanol, isopropanol or acetone, may be present up to 5% by weight, preferably up to 2% by weight. This may be of use in individual cases for lowering the surface tension or for preventing microbiological contamination. Preferably, however, no organic solvents may be present.

The term "dispersion or solution" refers to the fact that the substances present may in their totality be present either in dispersed form, dissolved form or else partly dispersed or dissolved in an intermediate state. The aqueous dispersion or solution preferably may have a pH of from 6.0 to 10.0, in particular from 6.5 to 9.0. In this pH range, the (meth)acrylate copolymers present may be predominantly in dispersed or at least partly dissolved form. Plasticizers are generally present in dissolved form. Other additives or auxiliaries, such as, for example, talc, may be present in dispersed form.

Solids Content

The solids content of the aqueous dispersion or solution may be more than 25% by weight, preferably more than 30% by weight, in particular 32-36% by weight. For comparison, the solids contents of dispersions or solutions which are used in spraying processes are generally only around 20% by weight.

The solids content may be used in particular together with the viscosity for controlling the balance between good wettability of the as yet uncoated capsule halves in the dipping process and acceptable drying time of the coated capsule halves after the dipping process. If the solids content is too low, the drying times may become too long, and, moreover, as a rule no adequate viscosity may be built up. If the solids content is too high, this may lead to drop formations on the dipsticks and to overall uneven coatings. Consequently, no exact adjustment of the layer thickness is possible.

Viscosity

File viscosity of the aqueous dispersion or solution may be 150 to 1500, preferably 180 to 1000, in particular 200 to 350 mPa·s. The viscosity may be determined, for example, using a Brookfield rotary viscometer. The determination method is known to the person skilled in the art (see e.g. ISO 3219: 1993).

Elongation at Break

The elasticity of the dried polymer film may essentially be characterized by its elongation at break. A dried film produced from the dispersion or solution according to the invention, e.g. by pouring, has an elongation at break of at least 200, preferably at least 250%. The elongation at break in [%] can be determined on sample films in accordance with DIN 53 455.

(Meth)Acrylate Copolymers

The aqueous dispersion or solution comprises a polymer mixture of at least one first (meth)acrylate copolymer, which is enteric, and at least one further (meth)acrylate copolymer, which is enteric or water-insoluble.

At least one first (meth)acrylate copolymer means one or more first (meth)acrylate copolymers.

At least one further (meth)acrylate copolymer means one or more further (meth)acrylate copolymers.

The polymer mixture comprises or consists of at least two (meth)acrylate copolymers. Preferably, the polymer mixture comprises or consists of two (meth)acrylate copolymers.

The first (meth)acrylate copolymer, which is enteric, and the further (meth)acrylate copolymer, which is enteric or water-insoluble, are preferably present in a ratio of from 2:1 to 1:2.

The first (meth)acrylate copolymer, which is enteric, and the further (meth)acrylate copolymer, which is enteric or water-insoluble, constitute preferably at least 45% by weight, particularly preferably at least 60% by weight, in particular at least 70% by weight, of the solid present in the dispersion.

An enteric (meth)acrylate copolymer may be understood as meaning those (meth)acrylate copolymers which are insoluble in the pH range of gastric fluid, pH 1.0 to 5.0, but dissolve in the pH range of the intestinal fluid, above pH 5.0, in particular pH 5.5 to 8.0. In particular, enteric coated drug forms in 0.1 N HCl release at most 10% of the active ingredient present over the course of 2 hours. Enteric (meth)acrylate copolymers are synonymous with (meth)acrylate copolymers which are composed of $C_1$- to $C_4$-alkyl esters of acrylic acid or methacrylic acid and have at least 5%, preferably 5 to 70%, in particular 8 to 60%, of monomer radicals with anionic groups, as a rule methacrylic acid radicals. $C_1$- to $C_4$-alkyl esters of acrylic acid or methacrylic acid may be in particular methyl methacrylate, ethyl methacrylate, butyl methacrylate, methyl acrylate, ethyl acrylate and butyl acrylate.

First Enteric (Meth)Acrylate Copolymer

Preferably, the first enteric (meth)acrylate copolymer may be an anionic (meth)acrylate copolymer. Preferably, the glass transition temperature of the first (meth)acrylate copolymer in accordance with ISO 11357-2, point 3.3.3, is more than 70° C.

Preferably, the first enteric (meth)acrylate copolymer is a polymer of 40 to 60% by weight of methacrylic acid and 60 to 40% by weight of methyl methacrylate or 60 to 40% by weight of ethyl acrylate (grade EUDRAGIT® L100 or EUDRAGIT® L100-55).

Of suitability in particular is EUDRAGIT® L100-55, which is a copolymer of 50% by weight of ethyl acrylate and 50% by weight of methacrylic acid.

Likewise suitable may be anionic (meth)acrylate copolymers of 20 to 40% by weight of methacrylic acid and 80 to 60% by weight of methyl methacrylate (grade EUDRAGIT® S).

Further (Meth)Acrylate Copolymer

The further (meth)acrylate copolymer may be enteric or water-insoluble. If the further (meth)acrylate copolymer is an enteric polymer, it is different from the first enteric (meth)acrylate copolymer.

Further Anionic (Meth)Acrylate Copolymer

Preferably, the further (meth)acrylate copolymer may be an enteric, anionic polymer which is different from the first enteric (meth)acrylate copolymer. Preferably, the glass transition temperature of the further (meth)acrylate copolymer in accordance with ISO 11357-2, point 3.3.3, is at most 70, preferably at most 60, in particular at most 50° C., e.g. 40 to 60° C.

Of particular suitability may be, for example, a polymer of 10 to 30% by weight of methyl methacrylate, 50 to 70% by weight of methyl acrylate and 5 to 15% by weight of methacrylic acid (grade EUDRAGIT® FS).

Specifically, for example EUDRAGIT® FS, which is a copolymer of 25% by weight of methyl methacrylate, 65% by weight of methyl acrylate and 10% by weight of methacrylic acid, may be suitable. EUDRAGIT® FS 30 D is a dispersion comprising 30% by weight of EUDRAGIT® FS.

Also suitable for the purposes of the invention may be a (meth)acrylate copolymer (see WO 2003/072087), which is composed of
- 20 to 34% by weight of methacrylic acid and/or acrylic acid,
- 20 to 69% by weight of methyl acrylate and
- 0 to 40% by weight of ethyl acrylate and/or optionally
- 0 to 10% by weight of further vinylically copolymerizable monomers, with the proviso that the glass transition temperature of the (meth)acrylate copolymer in accordance with ISO 11357-2, point 3.3.3, may be at most 60° C. This (meth)acrylate copolymer may have, in particular very good elongation at break properties.

The copolymer may be composed in particular of free-radically polymerized units of 20 to 34, preferably 25 to 33, particularly preferably 28 to 32% by weight of methacrylic acid or acrylic acid, preferably methacrylic acid, 20 to 69, preferably 35 to 65, particularly preferably 35 to 55% by weight of methyl acrylate and optionally 0 to 40, preferably 5 to 35, particularly preferably 15 to 35% by weight of ethyl acrylate together, with the proviso that the glass transition temperature of the copolymer (measurement without the addition of plasticizer at a residual monomer content (REMO) of less than 100 ppm, heating rate 10° C./min, nitrogen atmosphere) in accordance with ISO 11357-2, point 3.3.3 ($T_{mg}$), is at most 60, preferably 40 to 60, particularly preferably 45 to 55° C.

The copolymer preferably may contains exclusively the monomers methacrylic acid, methyl acrylate and ethyl acrylate in the quantitative fractions given above.

However, it may be additionally possible, without leading to an impairment of the essential properties, for small amounts in the range from 0 to 10, e.g. 1 to 5% by weight of further vinylically copolymerizable monomers, such as, for example, methyl methacrylate, butyl methacrylate, butyl acrylate or hydroxyethyl methacrylate, to be present.

Glass transition temperature here is to be understood in particular as meaning the midpoint temperature $T_{mg}$ in accordance with ISO 11357-2, point 3.3.3. Measurement takes place without the addition of plasticizer, at residual monomer contents (REMO) of less than 100 ppm, at a heating rate of 10° C./min and under a nitrogen atmosphere.

Also suitable for the purposes of the invention may be (meth)acrylate copolymers (see WO 2004/096185) comprising
- 20 to 33% by weight of methacrylic acid and/or acrylic acid,
- 5 to 30% by weight of methyl acrylate and
- 20 to 40% by weight of ethyl acrylate and
- greater than 10 to 30% by weight of butyl methacrylate and optionally
- 0 to 10% by weight of further vinylically copolymerizable monomers, where the fractions off the monomers add up to 100% by weight, with the proviso that the glass transition temperature of the copolymer in accordance with ISO 11357-2, point 3.3.3 (midpoint temperature $T_{mg}$) is 55 to 70° C. Because of good mechanical properties, copolymers of this type are particularly suitable for compressing pellets to give tablets.

The aforementioned copolymer may be composed in particular of free-radically polymerized units of
- 20 to 33% by weight, preferably 25 to 32% by weight, particularly preferably 28 to 31% by weight, of methacrylic acid or acrylic acid, preferably methacrylic acid,
- 5 to 30% by weight, preferably 10 to 28% by weight, particularly preferably 15 to 25% by weight, of methyl acrylate,
- 20 to 40% by weight, preferably 25 to 35% by weight, particularly preferably 28 to 32% by weight, of ethyl acrylate, and
- greater than 10 to 30% by weight, preferably 15 to 25% by weight, particularly preferably 18 to 22% by weight, of butyl methacrylate, where the monomer composition is selected so that the glass transition temperature of the copolymer is 55 to 70° C., preferably 59 to 66° C., particularly preferably 60 to 65° C.

The copolymer preferably contains exclusively, up to 90, 95 or 99 to 100% by weight including all weights and sub-weights therebetween, of the monomers methacrylic acid, methyl acrylate, ethyl acrylate and butyl methacrylate in the quantitative ranges stated above.

However, it may also be possible, without leading to an impairment of the essential properties of the invention, for small amounts in the range from 0 to 10, e.g. 1 to 5% by weight of further vinylically copolymerizable monomers, such as, for example, methyl methacrylate, butyl acrylate, hydroxyethyl methacrylate, vinylpyrrolidone, vinylmalonic acid, styrene, vinyl alcohol, vinyl acetate and/or derivatives thereof, to be present.

Water-Insoluble (Meth)Acrylate Copolymers

Within the context of the invention, a water-insoluble (meth)acrylate copolymer may be understood as meaning those (meth)acrylate copolymers which are water-insoluble or merely water-swellable over the entire pH range from 1 to 14. These are preferably "neutral" (meth)acrylate copolymers. Neutral may be understood as meaning that the (meth)acrylate copolymers are composed predominantly or completely of neutral monomers, e.g. to more than 95% by weight, to more than 98% by weight, to more than 99% by weight or to 100% by weight. Accordingly, the term "neutral" does not entirely rule out the presence of ionic groups in the polymer. (Meth)acrylate copolymers with a content of less than 5% by weight, preferably less than 2% by weight, preferably less than 1% by weight, of ionic, in particular anionic groups, are referred to as "neutral" within the context of the invention or as "essentially neutral". These neutral or essentially neutral, or optionally only to a small extent, ionic polymers are water-insoluble or merely water-swellable and have no enteric properties.

The further (meth)acrylate copolymer may preferably be a water-insoluble polymer which may be a polymer of 20 to 40% by weight of ethyl acrylate, 60 to 80% by weight of methyl methacrylate and less than 5% by weight, preferably less than 2% by weight, preferably less than 1% by weight, of methacrylic acid (grade EUDRAGIT® NE or EUDRAGIT® NM).

For example, EUDRAGIT® NE, which a copolymer of 30% by weight of ethyl acrylate and 70% by weight of methyl methacrylate, may be suitable.

Auxiliaries which Influence the Viscosity of the Dispersion or Solution and the Elasticity of the Dried Polymer Film The viscosity of the dispersion and the elasticity or the elongation at break of the dried polymer film may usually not be brought into the required ranges by the polymer mixture alone. Consequently, the aqueous dispersion or solution may additionally comprise auxiliaries which, together with the polymer mixture, influence or increase and steer into the required ranges the viscosity of the dispersion and the elasticity of the dried polymer film.

A comparatively strong influencing of said parameters may be achieved in particular through the addition of plasticizers or basic substances. These auxiliaries may preferably constitute at most 30% by weight, in particular at most 20% by weight, of the solid present in the dispersion. The content of these auxiliaries may be, for example, 5 to 30% by weight, preferably 10 to 20% by weight, of the solid present in the dispersion.

Plasticizers

Plasticizers may contribute to influencing and/or increasing the viscosity of the dispersion and the elasticity of the dried polymer film.

Substances suitable as plasticizers generally have a molecular weight ($M_w$) between 100 and 20 000 and contain one or more hydrophilic groups in the molecule, e.g. hydroxyl, ester or amino groups. Citrates, phthalates, sebacates, castor oil may be suitable. Examples of suitable plasticizers may be alkyl esters of citric acid, propylene glycol, glycerol esters, alkyl esters of phthalic acid, alkyl esters of sebacic acid, sucrose esters, sorbitan esters, diethyl sebacate, dibutyl sebacate and polyethylene glycol 300 to 35 000. Preferred plasticizers may be tributyl citrate, triethyl citrate, acetyltriethyl citrate, dibutyl sebacate and diethyl sebacate. The use amounts of plasticizers may be in the range from 1 and 30, preferably 5 to 25% by weight, based on the polymer mixture. Preference may be given to polyethylene glycols with a high molecular weight, in particular polyethylene glycol 20 000 or polyethylene glycol 35 000, which can greatly increase the viscosity of the dispersion or solution.

Preferably, the use amounts for polyethylene glycol 20 000 or polyethylene glycol 35 000 may be 5 to 25, in particular 10 to 20% by weight, based on the polymer mixture. Additionally, other plasticizers, such as, for example, triethyl citrate, in amounts of from 5 to 15% by weight based on the polymer mixture, may be combined with polyethylene glycol 20 000 or polyethylene glycol 35 000.

Basic Substances

Basic substances may contribute to influencing or increasing the viscosity of the dispersion and the elasticity of the dried polymer film.

In order to prepare an aqueous solution of the enteric (meth)acrylate copolymer, a partial or complete neutralization of the acid groups may be generally necessary. The first or optionally also a further enteric (meth)acrylate copolymer may, for example, be gradually stirred into water and in so doing may be partially or completely neutralized by adding a basic substance, such as, for example, NaOH, KOH, ammonium hydroxide or organic bases, such as, for example, triethanolamine. It may also be possible to use a powder of the copolymer to which a base, e.g. NaOH, may have already been added during its preparation for the purpose of (partial) neutralization, meaning that the powder is an already (partially) neutralized polymer. Particular preference is given to sodium hydroxide solution or NaOH.

Further suitable basic substances may be, for example: sodium carbonate, potassium carbonate, sodium picarbonate, trisodium phosphate, trisodium citrate or ammonia or physiologically compatible amines, such as triethanolamine or tris(hydroxymethyl)aminomethane, the cationic, basic amino acids histidine, arginine and/or lysine, natural or synthetic oligomers or polymers, e.g. of 3 to 100, preferably 5 to 25, units, of histidine, arginine or lysine, polyhistidines, polyarginines, polylysines, cationic or zwitterionic phospholipids, such as, for example, phosphatidylcholine, ribonucleosides, condensation products of the hydroxyl function on carbon atom 1 of ribose with the heterocyclic amino function of the bases adenine, guanine, cytosine, thymine or uracil, corresponding to the occurrence in RNA, or deoxyribonucleosides, condensation products of the hydroxyl function on carbon atom 1 of deoxyribose with the heterocyclic amino function of the bases adenine, guanine, cytosine, thymine or uracil, corresponding to the occurrence in DNA.

Preference may be given to a degree of neutralization of from 3 to 12 mol % of the anionic groups at least of the (meth)acrylate copolymer. Preferably, the neutralization takes place with sodium hydroxide in the form of 1.5 to 2 normal sodium hydroxide solution. The relatively high concentration of the sodium hydroxide solution prevents too great a reduction in the solids content. The partial neutralization may be accompanied by a thickening of the dispersion or solution, i.e. an increase in the viscosity.

The quantitative fraction of basic substances of the total content of the auxiliaries which influence or increase the viscosity of the dispersion and the elasticity of the dried polymer film may be more likely to be low compared to plasticizers. The influence of the basic substances in particular on the viscosity, however, may be relatively great, meaning that even these comparatively small amounts bring about significant effects. Preference may be given to using a combination of plasticizers and basic substances.

Further Pharmaceutically Customary Auxiliaries which are not Plasticizers or Bases Optionally, further pharmaceutically customary auxiliaries, which are not plasticizers or bases, but which may be also used in the fields of food supplements and cosmetics, may be present in amounts of, for example, at most 25% by weight, at most 10% by weight, or at most 5% by weight, based on the total solids content of the dispersion or solution. Compared to the plasticizers or the bases, these further pharmaceutically customary auxiliaries only influence the viscosity of the dispersion or solution and the elasticity of the dried polymer film to a low degree, if at all.

Here, mention may be to be made, for example, of antioxidants, dyes, flavourings, lustre agents, lubricants, such as, for example, talc, wetting agents, pigments, stabilizers, sweeteners etc. These serve primarily as processing auxiliaries and are intended primarily to ensure, for example, a safe and reproducible production process, good long-term storage stabilities, a pleasant appearance or the identifiability.

In particular, pigments require particular mention. In order to be covering, pigments may be added, for example, in relatively high concentrations, for example in amounts of from 10 to 25% by weight, based on the total solids content of the dispersion or solution. In this large amount and depending on the pigment used, an at least slight, measurable influence on the viscosity of the dispersion or the elasticity of the dried polymer film is usually observed. When adding large amounts of pigments, the viscosity will possibly increase whereas the elasticity of the dried polymer film generally ought to decrease. However, this may be compensated through a slight shift in the type and quantitative ratios of the other components which, for their part, have a relatively great influence on the viscosity of the dispersion or the elasticity of the dried polymer film, the polymer mixture, and, optionally, plasticizers or bases.

Further auxiliaries which are not plasticizers or bases and which are also not pigments are, if present at al, generally present in much lower concentrations, e.g. less than 10% by weight, less than 5% by weight or less than 2% by weight, based on the total solids content of the dispersion or solution. Consequently, these further auxiliaries may merely influence the viscosity of the dispersion or the elasticity of the dried polymer film in a negligible manner or only to a very slight extent.

Preferably, only plasticizers and/or bases and also optionally pigments are present as auxiliaries.

Dipping Process

The dipping processes or dip coating processes for producing capsule halves and for the enteric coating of capsule halves are conventionally known (see in this regard e.g.: Fahrig W. and Hofer U. (1983): *Die Kapsel, Grundlagen, Technologie and Biopharmazie einer modernen Arzneiform* [Capsules, Principles, Technology and Biopharmacy of a Modern Drug Form], Wissenschaftliche Verlagsgesellschaft mbH Stuttgart).

Capsule halves may be produced by dipping sticks into viscous solutions, e.g. gelatine solutions. The sticks are then removed from the viscous solution. The viscous solution dries on the sticks. The capsule halves are cut off straight from the sticks using a cutting tool and then removed from the sticks. Since matching upper and lower parts of capsules have different sizes and geometries, they are produced separately.

The process for the enteric coating of capsule halves may be integrated into the dipping process for producing capsule halves by, in an additional step, dipping the capsule halves dried on the dipsticks into the coating composition according to the invention. In an analogous manner, the enteric coated capsule halves are cut off straight from the sticks using a cutting tool and are then removed from the sticks.

Process

The invention furthermore relates to a process for producing enteric coated capsule halves in the dipping process according to the following operations:

dipping uncoated capsule halves on dipsticks into a coating composition according to the invention, removing the sticks with the enteric coated capsule halves, drying the coating composition, cutting off the coated capsule halves on the sticks by means of a cutting tool and removing the enteric coated capsule halves from the sticks.

The invention relates to the use of a coating composition according to the invention for the enteric coating of capsule halves in the dipping process. The enteric coated capsule halves may be used for producing capsules filled with active ingredients or food supplements for oral applications in the fields of pharmacy, food supplements or cosmetics.

Having generally described this invention, a further understanding can be obtained by reference to certain specific examples which are provided herein for purposes of illustration only, and are not intended to be limiting unless otherwise specified.

EXAMPLES

First (Meth)Acrylate Copolymer

EUDRAGIT® L100-55 is a copolymer of 50% by weight of ethyl acrylate and 50% by weight of methacrylic acid.

Further (Meth)Acrylate Copolymers

EUDRAGIT® FS is a copolymer of 25% by weight of methyl methacrylate, 65% by weight of methyl acrylate and 10% by weight of methacrylic acid. EUDRAGIT® FS 30 D is a dispersion comprising 30% by weight of EUDRAGIT® FS.

EUDRAGIT® NE is a copolymer of 30% by weight of ethyl acrylate and 70% by weight of methyl methacrylate.

Auxiliaries which Influence the Viscosity of the Dispersion and the Elasticity of the Dried Polymer Film:

Polyethylene glycol 35 000 (PEG 35 000) and triethyl citrate (TEC), and NaOH (for the partial neutralization of EUDRAGIT® L100-55/EUDRAGIT® L 30 D55).

Formulations:

A partially neutralized redispersion of EUDRAGIT® L 100-55 served as the basis for all examples and as comparative examples. This had the purpose of achieving a somewhat higher solids concentration than with standard commercial EUDRAGIT®L 30 D-55.

For this, 300 g of EUDRAGIT® L 100-55 were incorporated into 650 g of demineralized water through slow addition by means of a propeller stirrer. After stirring for 30 minutes, 50 g of 2 N NaOH solution were then slowly added in order to produce a dispersion with a solids content of 30.4%. The degree of partial neutralization corresponded to about 6 mol % of the anionic groups present in the copolymer. The following final mixtures were prepared using this base formulation. Standard commercial hard gelatine capsule shells were coated therewith by dipping with subsequent drying.

The results of Examples 1 to 3 and Comparative Examples C4 to C7 are summarized in the table below.

TABLE

| | Example | | | | | | |
|---|---|---|---|---|---|---|---|
| | 1 | 2 | 3 | C4 | C5 | C6 | C7 |
| EUDRAGIT ® L 100-55 dispersion with 30-4% solids | 100 | 100 | 100 | 100 | 100 | / | / |
| EUDRAGIT ® FS 30 D | / | 100 | 100 | / | / | 100 | 100 |
| EUDRAGIT ® NE 30 D | 100 | / | / | / | / | / | / |
| PEG 35 000 (% of polymer) | 15 | 15 | 15 | / | 30 | / | / |
| PEG 20 000 (% of polymer) | / | / | / | 20 | / | / | / |
| TEC (% of polymer) | / | 5 | 10 | / | / | 10 | 20 |
| Viscosity [mpa · s] | 801 | 316 | 290 | 70 | 8700 | 70 | 70 |
| Elongation at break [%] | 430 | 261 | 398 | 34 | 225 | 394 | 1236 |
| Dissolution of sample capsule at pH 6.8 | 25-30 min | 15-20 min | 15-20 min | 15-20 min | 15-20 min | >60 min | >60 min |
| solids content [% by wt.] | 33.2 | 34.2 | 35.1 | 34.3 | 36.1 | 32.0 | 34.0 |

TABLE-continued

| | Example | | | | | |
|---|---|---|---|---|---|---|
| | 1 | 2 | 3 | C4 | C5 | C6 |
| Brittleness of the sample capsule | +++ | + | ++ | --- | - | ++ | +++ |

% of polymer = % by weight, based on the polymer or polymers
+++ = ideal,
++ = good,
+ just acceptable,
− = too thick and nonuniform,
−−− = very brittle U.S. Provisional Application No. 61/229,537, filed Jul. 29, 2009, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. An enteric coated capsule half, comprising a water soluble or water swellable polymer material,
wherein the enteric coated capsule half is a lower half or an upper half of a capsule, in which a lower half and an upper half each comprise a water soluble or water swellable polymer material and fit together such that they may be engaged in one another in a locking manner to form a closed capsule, the lower half and an upper half each coated continuously on an entirety of an outside thereof with an enteric coating comprising a polymer mixture of at least one first enteric (meth)acrylate copolymer and at least one further enteric or water soluble (meth)acrylate copolymer, and at least one auxiliary;
the coating has an elasticity measured by elongation at break of at least 200%,
the coating confers a property to the capsule, such that, when closed, the capsule does not dissolve in 0.1 N HCl at pH 1.2 after two hours, but does dissolve completely in a buffer solution at pH 6.8 in less than 30 minutes,
the coating is obtained from a process comprising dipping a capsule half into a coating composition which is a solution or dispersion of the polymer mixture having a solids content of more than 25% by weight and a viscosity of from 150 to 1500 mPas, and
the coating on a portion of the outside of the lower half that is overlapped by the upper half is configured to seal any gap between the enteric coated capsule half and a further capsule half when overlapping or being overlapped by the further capsule half.

2. The enteric coated capsule half according to claim 1, wherein at least 45% by weight of the solids content in the coating composition is the weight of the polymer mixture of at least one first enteric (meth)acrylate copolymer and at least one further enteric or water soluble (meth)acrylate copolymer.

3. The enteric coated capsule half according to claim 1, comprising gelatine or hydroxypropylmethyl cellulose.

4. The enteric coated capsule half according to claim 1, wherein the at least one first, enteric (meth)acrylate copolymer is a polymer obtained from a monomer composition comprising:

40 to 60% by weight of methacrylic acid, and
60 to 40% by weight of methyl methacrylate or 60 to 40% by weight of ethyl acrylate.

5. The enteric coated capsule half according to claim 1, wherein the at least one further enteric or water soluble (meth)acrylate copolymer is a polymer obtained from a monomer composition comprising:
10 to 30% by weight of methyl methacrylate;
50 to 70% by weight of methyl acrylate; and
5 to 15% by weight of methacrylic acid.

6. The enteric coated capsule half according to claim 1, wherein the at least one auxiliary is at least one plasticizer, at least one basic substance or a mixture thereof.

7. The enteric coated capsule half according to claim 1, wherein the at least one auxiliary is a polyethylene glycol.

8. The enteric coated capsule half according to claim 1, wherein the composition is a solution or dispersion of the polymer mixture having a solids content of more than 30% by weight.

9. The enteric coated capsule half according to claim 1, wherein the composition is a solution or dispersion of the polymer mixture having a solids content of from 32 to 36% by weight.

10. The enteric coated capsule half according to claim 1, wherein a thickness of the coating is from 20 to 100 μm.

11. The enteric coated capsule half according to claim 1, wherein a thickness of the coating is from 40 to 80 μm.

12. The enteric coated capsule half of claim 1, wherein the enteric coated capsule half is configured to overlap the further capsule half.

13. The enteric coated capsule half of claim 1, wherein the enteric coated capsule half is configured to be overlapped by the further capsule half.

14. An enteric capsule, comprising:
two joined overlapping capsule halves comprising a first half and a second half,
wherein
the first half is the enteric coated capsule half of claim 1, and
a portion of the coating between the two joined capsule halves seals any gap between the capsule halves.

15. The enteric capsule according to claim 14, wherein no further sealing is applied to seal any gap between the capsule half and another capsule half.

16. The enteric capsule according to claim 14, wherein the second half also comprises the coating on at least a portion of a surface of the second half.

17. The enteric capsule according to claim 14, wherein the second half partly overlaps a portion of the first half.

18. The enteric capsule according to claim 14, wherein the first half partly overlaps a portion of the second half.

19. The enteric coated capsule half according to claim 1, wherein the at least one basic substance is sodium hydroxide.

20. The enteric coated capsule half according to claim 1, wherein a weight ratio of the at least one first enteric (meth)acrylate copolymer to the at least one further enteric or water soluble (meth)acrylate copolymer is from 2:1 to 1:2.

21. A method for preparing the enteric coated capsule half of claim 1, the method comprising:
    dipping an uncoated capsule half on a dipstick into the coating composition thereby obtaining an enteric coated capsule half;
    removing the stick with the enteric coated capsule half from the enteric coating composition;
    drying the enteric coating composition;
    cutting off the enteric coated capsule half; and
    removing the enteric coated capsule half from the stick.

22. The method of claim 21, wherein the at least one first, enteric (meth)acrylate copolymer is a polymer obtained from a monomer composition comprising:
    40 to 60% by weight of methacrylic acid, and
    60 to 40% by weight of methyl methacrylate or 60 to 40% by weight of ethyl acrylate.

23. The method of claim 21, wherein the at least one further enteric or water soluble (meth)acrylate copolymer is a polymer obtained from a monomer composition comprising:
    10 to 30% by weight of methyl methacrylate;
    50 to 70% by weight of methyl acrylate; and
    5 to 15% by weight of methacrylic acid.

24. The method of claim 21, wherein the at least one auxiliary is at least one plasticizer, at least one basic substance or a mixture thereof.

25. The method of claim 21, wherein the at least one auxiliary is a polyethylene glycol.

26. The method of claim 21, wherein the at least one basic substance is sodium hydroxide.

27. The method of claim 21, wherein a weight ratio of the at least one first enteric (meth)acrylate copolymer to the at least one further enteric or water soluble (meth)acrylate copolymer is from 2:1 to 1:2.

* * * * *